(12) United States Patent
Sablone et al.

(10) Patent No.: US 10,479,022 B2
(45) Date of Patent: Nov. 19, 2019

(54) APPARATUS FOR THE TRANSVERSE WELDING OF A MOVING TAPE

(71) Applicant: Fameccanica.Data S.p.A., Pescara (IT)

(72) Inventors: Gabriele Sablone, Pescara (IT); Oscar Centorame, Giulianova (IT)

(73) Assignee: FAMECCANICA.DATA S.p.a, Pescara (IT)

( * ) Notice: Subject to any disclaimer, the term of this patent is extended or adjusted under 35 U.S.C. 154(b) by 133 days.

(21) Appl. No.: 15/863,640

(22) Filed: Jan. 5, 2018

(65) Prior Publication Data

US 2018/0207877 A1     Jul. 26, 2018

(30) Foreign Application Priority Data

Jan. 26, 2017   (IT) ........................ 102017000008422

(51) Int. Cl.
*A61F 13/00*     (2006.01)
*B29C 65/00*     (2006.01)
(Continued)

(52) U.S. Cl.
CPC ........ *B29C 65/02* (2013.01); *A61F 13/15739* (2013.01); *B29C 65/087* (2013.01);
(Continued)

(58) Field of Classification Search
CPC .......... A61F 13/00; A61F 13/10; A61F 13/15; A61F 13/157; A61F 13/1573;
(Continued)

(56) References Cited

U.S. PATENT DOCUMENTS

| 4,758,293 A | * | 7/1988 | Samida .................. B29C 65/08 156/308.4 |
| 5,660,679 A | * | 8/1997 | Rajala ................. B29C 66/8221 156/580.1 |
| 2010/0096065 A1 | * | 4/2010 | Yamamoto ........ A61F 13/15739 156/73.4 |

FOREIGN PATENT DOCUMENTS

| JP | 2005212149 A | 8/2005 |
| JP | 6002867 B1 | 10/2016 |
| WO | 02078935 A1 | 10/2002 |

OTHER PUBLICATIONS

Italian Search Report and Written Opinion dated Sep. 22, 2017 for Application No. 201700008422.

* cited by examiner

*Primary Examiner* — Jacob T Minskey
*Assistant Examiner* — Matthew Hoover
(74) *Attorney, Agent, or Firm* — Patterson + Sheridan, LLP

(57) ABSTRACT

An apparatus for the transverse welding of a tape traveling in a machine direction, comprising: a stationary structure, a rotary structure rotatable with respect to the stationary structure about a rotation axis perpendicular to said machine direction, a plurality of welding units carried by said rotary structure and spaced apart in a circumferential direction, wherein each of said welding units comprises an inner welding element fixed relative to the rotary structure and an outer welding element cyclically movable with respect to the rotary structure between a release position and an operative position, and vice versa, wherein each of said outer welding elements during the movement from said release position to said operative position, and vice versa, performs an angular rotation movement about a respective radial axis perpen- (Continued)

dicular to said rotation axis, and a linear translation movement along said radial axis.

9 Claims, 4 Drawing Sheets

(51) Int. Cl.
    *B29C 65/02*     (2006.01)
    *B29C 65/78*     (2006.01)
    *A61F 13/15*     (2006.01)
    *B29C 65/08*     (2006.01)
    *B29L 31/48*     (2006.01)

(52) U.S. Cl.
    CPC ...... *B29C 65/7847* (2013.01); *B29C 65/7858* (2013.01); *B29C 65/7885* (2013.01); *B29C 66/1122* (2013.01); *B29C 66/431* (2013.01); *B29C 66/80* (2013.01); *B29C 66/81465* (2013.01); *B29C 66/83511* (2013.01); *A61F 2013/15869* (2013.01); *A61F 2013/15878* (2013.01); *B29C 66/8322* (2013.01); *B29L 2031/4878* (2013.01)

(58) Field of Classification Search
CPC ... A61F 13/15739; B29C 65/00; B29C 65/02; B29C 65/08; B29C 65/087; B29C 65/70; B29C 65/78; B29C 65/784; B29C 65/7847; B29C 65/785; B29C 65/7858; B29C 65/788; B29C 65/7885; B29C 66/00; B29C 66/10; B29C 66/11; B29C 66/112; B29C 66/1122; B29C 66/40; B29C 66/43; B29C 66/431; B29C 66/80; B29C 66/81; B29C 66/814; B29C 66/8146; B29C 66/81465; B29C 66/83; B29C 66/835; B29C 66/8351; B29C 66/83511
See application file for complete search history.

APPARATUS FOR THE TRANSVERSE WELDING OF A MOVING TAPE

CROSS-REFERENCE TO RELATED APPLICATIONS

This application claims benefit of Italian patent application number 102017000008422, filed Jan. 26, 2017 which is herein incorporated by reference.

BACKGROUND OF THE INVENTION

Field of the Invention

The present invention relates to an apparatus for the transverse welding of a tape traveling in a machine direction.

The invention has been developed, in particular, for application to machines for producing absorbent sanitary articles.

Description of Prior Art

In the field of production of absorbent sanitary articles, it is frequently necessary to perform transverse welding on composite tapes advancing in a machine direction. For example, producing the so-called "training pants" envisages forming a composite tape consisting of a continuous chain of product blanks in which the individual blanks are oriented in a direction transverse to the machine direction. The continuous composite tape is welded at regular intervals along directions transverse to the machine direction, to form closure lines, which extend along the sides of the individual articles, and which give the articles a pant-shape.

Modern machines for producing absorbent sanitary articles operate at extremely high speeds in the order of 800-1000 pieces/1'. Fundamentally, two technologies are used to weld the component materials used in the absorbent sanitary articles: thermal welding and ultrasonic welding. In order to carry out transverse welding lines on composite tapes moving at high speed with the aforesaid technologies, it is necessary that the welding elements remain in contact with the tape for the time necessary to transfer the welding energy from the welding elements to the moving tape. In the case of thermal welding, the moving tape is typically clamped between two heated welding elements. In the case of ultrasonic welding, the moving tape is clamped between a sonotrode and an anvil. In both cases, in order to carry out the welding it is necessary that the welding element and the anvil move together with the tape, in order to remain in contact with the moving tape for the time necessary to carry out the welding.

In the state of the art, various solutions are already known, which involve advancing a continuous composite sheet laid on the periphery of a rotary structure carrying a plurality of welding units spaced apart in a circumferential direction. The composite tape is arranged on the periphery of the rotary structure, which rotates about a rotation axis with a peripheral speed equal to the speed of the composite tape. Along the periphery of the rotary structure, the composite tape cooperates with a plurality of welding units, each of which comprises a first and a second welding element located, respectively, inside and outside the path of the tape.

Examples of welding apparatus of this type are described in WO 02/078935A1, U.S. Pat. Nos. 4,758,293 and 5,660,679.

In welding apparatus of this type, it is necessary that the outer welding element is movable between an engagement position, in which it cooperates with the inner welding element to carry out the transverse welding of the moving tape, and a release position, in which the outer welding element is displaced with respect to the path of the tape, to allow the inlet and outlet of the tape on the periphery of the rotary structure.

The document WO 02/078935A1 describes an ultrasonic welding apparatus comprising a drum, rotating about a rotation axis, and carrying a plurality of ultrasonic welding units spaced apart in a circumferential direction. Each ultrasonic welding unit comprises a sonotrode fixed relative to the drum, and an anvil movable between a clamping position and a retracted position. Each anvil is articulated to the drum about a respective tangential axis, transverse to the rotation axis. A stationary cam is engaged by a plurality of cam followers attached to the respective anvils. During rotation of the drum about the rotation axis, the cam controls the oscillation movement of the anvils about the respective articulation axes between a raised position and a clamping position.

A drawback of this solution is that the anvil comes into contact with the tape first on the edge of the tape closest to the articulation axis of the anvil, and then with the edge of the tape furthest from the articulation axis of the anvil. Welding of the tape can only start when the tape is clamped between the anvil and the sonotrode. Therefore, the time required for lowering the anvil from the raised position to the lowered position results in an increase in the time for implementing the welding. Furthermore, the contact pressure is not uniform along the welding line since the contact pressure varies according to the distance from the articulation axis of the anvil.

The document U.S. Pat. No. 4,758,293 describes a solution in which the anvils are movable between an engagement position and a release position along a direction parallel to the rotation axis. This solution also involves a relatively long time to move the anvil from the release position to the engagement position, given that each anvil must complete a stroke equal to or greater than the width of the tape.

SUMMARY OF THE INVENTION

The present invention aims to provide an apparatus for the transverse welding of a moving tape, which overcomes the problems of the prior art.

In particular, the present invention aims to provide a welding apparatus in which the movement of the welding elements between the release position and the engagement position, and vice versa, occurs at high speed, and in which the welding elements are able to ensure a uniform contact pressure along the welding lines.

According to the present invention, this object is achieved by a welding apparatus having the characteristics forming the subject of claim 1.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Figure 1:
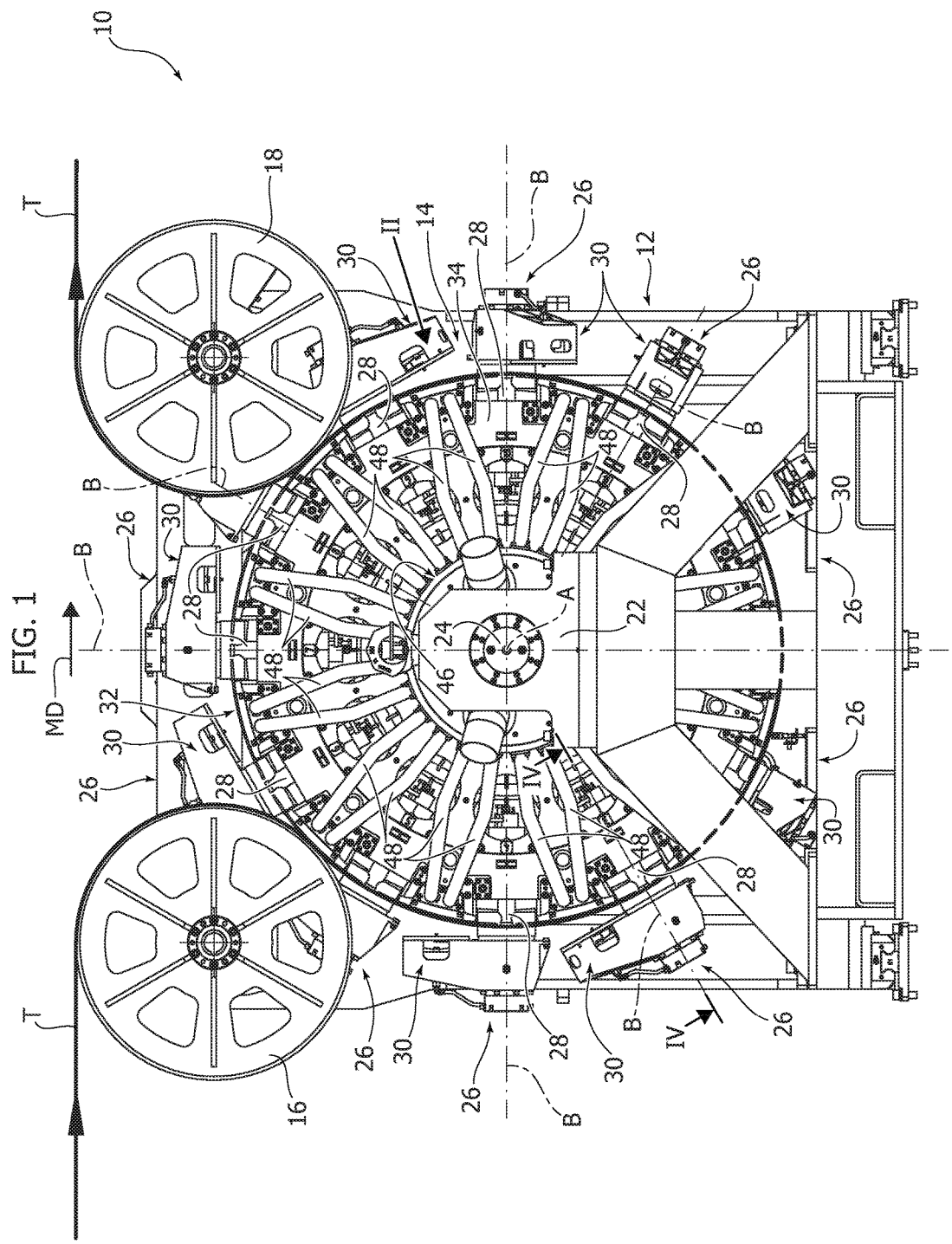
FIG. 1 is a front elevational view of a welding apparatus according to the present invention.

With reference to FIG. 1, numeral 10 indicates a welding apparatus for carrying out transverse welding on a moving tape T advancing in a machine direction MD.

The apparatus 10 comprises a stationary structure 12 and a rotary structure 14 rotatable with respect to the stationary structure 12 about a rotation axis A perpendicular to the machine direction MD. The apparatus 10 comprises a first wheel 16, which receives a tape T to be welded, advancing in the machine direction MD, and guides it on the periphery of the rotary structure 14, and a second wheel 18, which receives the welded tape T from the periphery of the rotary structure 14, and returns it to the machine direction MD.

Figure 2:
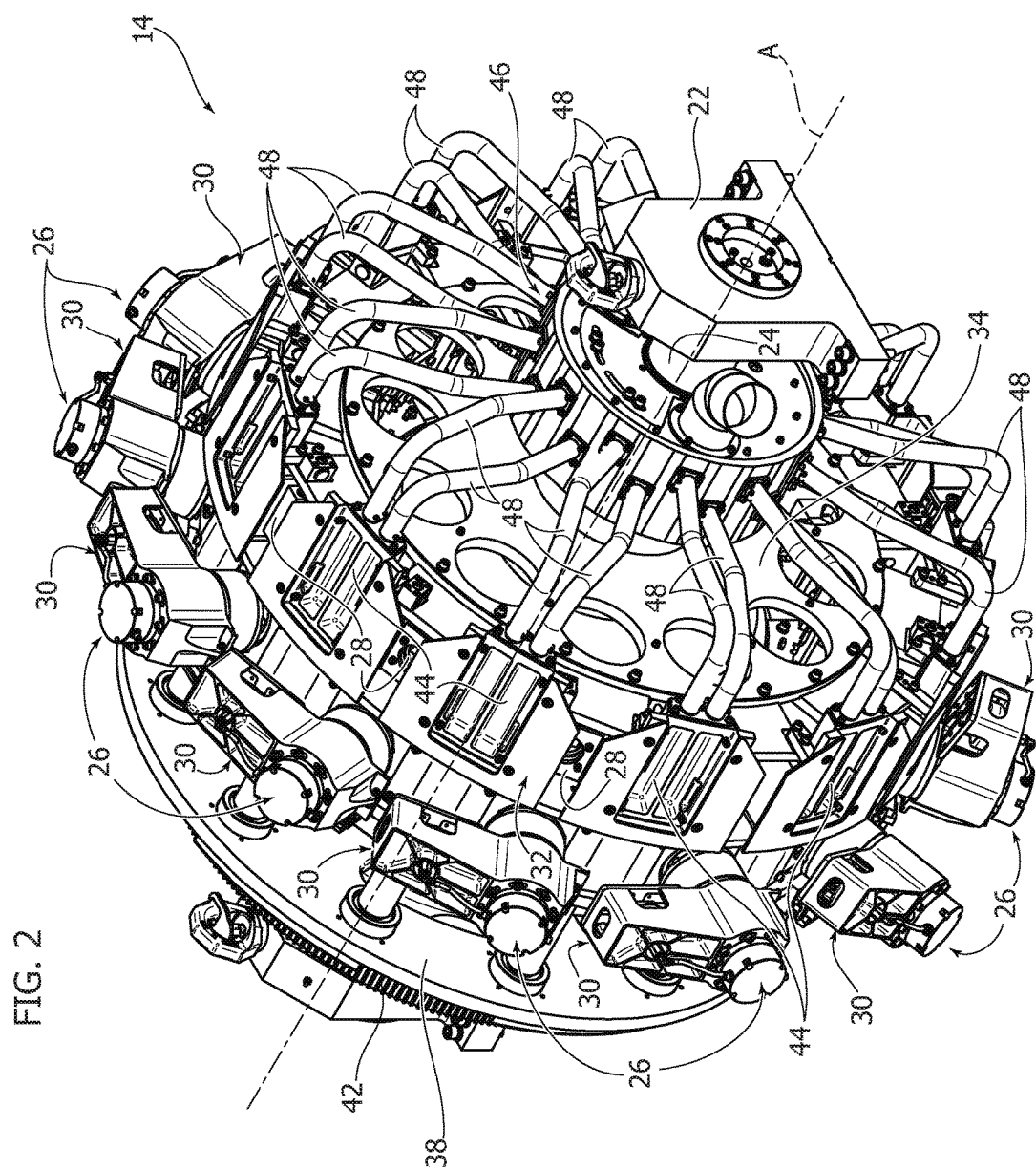
FIG. 2 is a perspective view of the part indicated by the arrow II in FIG. 1.
Figure 3:
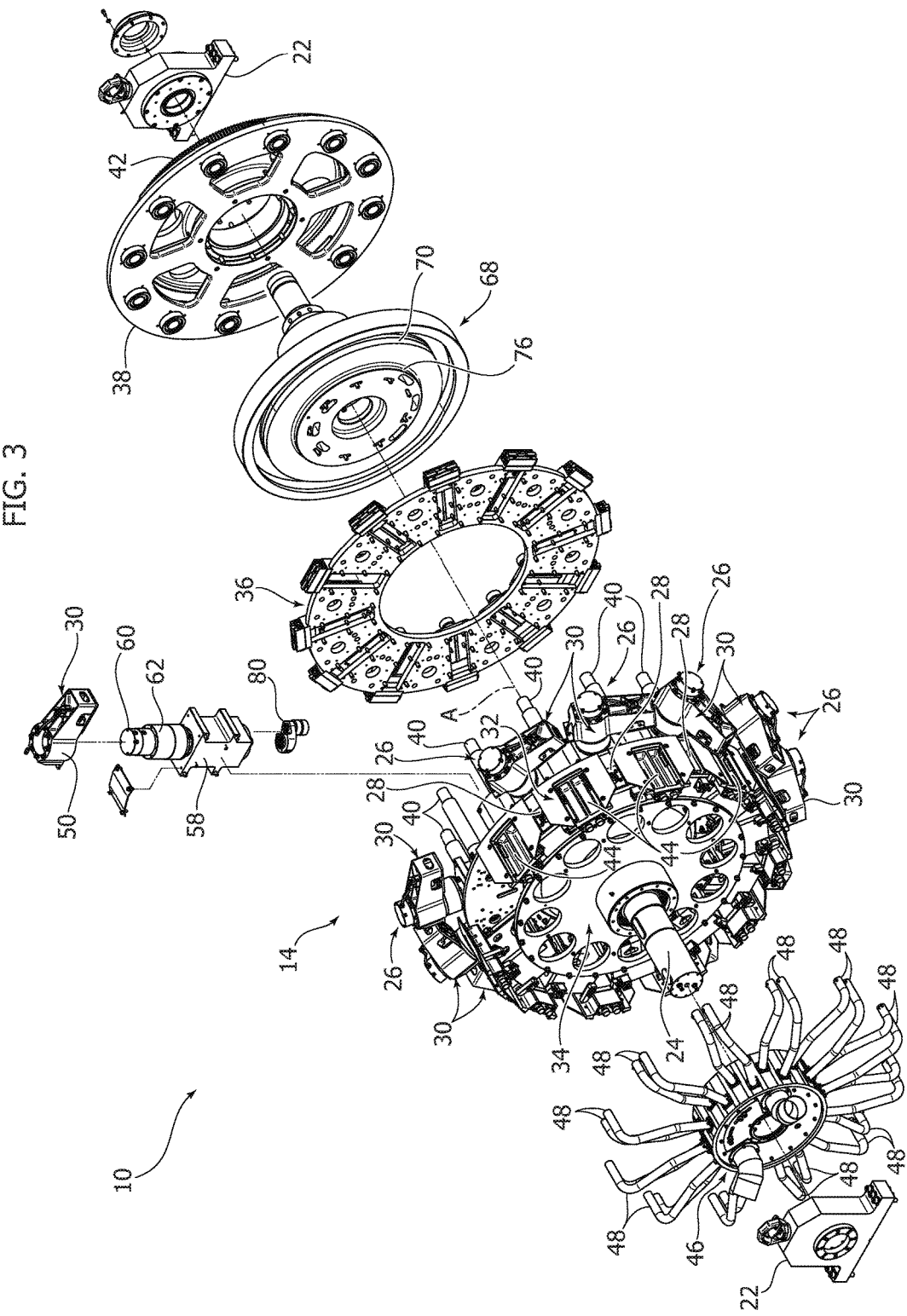
FIG. 3 is an exploded perspective view of some parts of the welding apparatus according to the invention.

With reference to FIGS. 1-3, the stationary structure 12 comprises an axle 24 supported at the ends by two supports 22, and coaxial with the rotation axis A.

With reference to FIGS. 1 and 2, the rotary structure 14 carries a plurality of welding units 26, angularly spaced apart from each other, by a distance typically constant in the circumferential direction. In the illustrated example, the rotary structure 14 carries twelve welding units 26 spaced apart angularly from each other by 30°. Each welding unit 26 comprises an inner welding element 28 and an outer welding element 30 arranged, respectively, inside and outside a perimeter wall 32 of the rotary structure 14 on which the tape T is retained during the welding path. The welding units 26 rotate together with the rotary structure 14 about the rotation axis A.

The welding units 26 can be thermal welding units or ultrasonic welding units. In the illustrated example, the welding units 26 are ultrasonic welding units. The inner welding elements 28 are sonotrodes facing respective windows of the perimeter wall 32 of the rotary structure 14, and the outer welding elements 30 are anvils configured to clamp the tape to be welded T against the respective sonotrodes 28. The sonotrodes 28 are electrically powered by means of a rotating electric collector, coaxial with the axis 24.

With reference to FIG. 3, the rotary structure 14 comprises a first support plate 34, a second support plate 36, and a drive plate 38. The plates 34, 36, 38 are fixed to each other, for example, by means of a plurality of pins 40 parallel to the rotation axis A. The drive plate 38 is fixed to a gear 42 driven by an electric motor, which controls the rotation of the rotary structure 14 about the axis A.

With reference to FIGS. 2 and 3, the perimeter wall 32 of the rotary structure 14 has a plurality of suction chambers 44 connected to a vacuum source by means of a rotary distributor 46. The rotary distributor 46 is connected to the suction chambers 44 by means of a plurality of conduits 48. The suction chambers 44 have the object of maintaining the tape T in contact with the periphery wall 32 of the rotary structure 14.

The outer welding elements 30 are cyclically movable with respect to the rotary structure 14 between a release position and an operative position. In the release position, the outer welding elements 30 are displaced laterally with respect to the path of the tape T so that the passage of the tape from the first wheel 16 to the perimeter wall 32, and the passage of the tape T from the perimeter wall 32 to the second wheel 18, are not hindered. In the operative position, the outer welding elements 30 press the tape T against the respective inner welding elements 28 with a predetermined radial force, in order to allow transfer of the welding energy from the welding elements 28, 30 to the tape T.

The movement between the release position and the operative position, and vice versa, of the outer welding elements 30 comprises an angular rotation movement about respective radial axes B and a linear translation movement in the direction of the aforesaid respective radial axes B. The radial axes B are perpendicular to the rotation axis A and each of the radial axes B, together with the rotation axis A, identifies a plane that contains them both; the set of the aforesaid planes, in turn, defines a bundle of planes where the rotation axis A is the straight line belonging to all the planes of the bundle.

Figure 4:
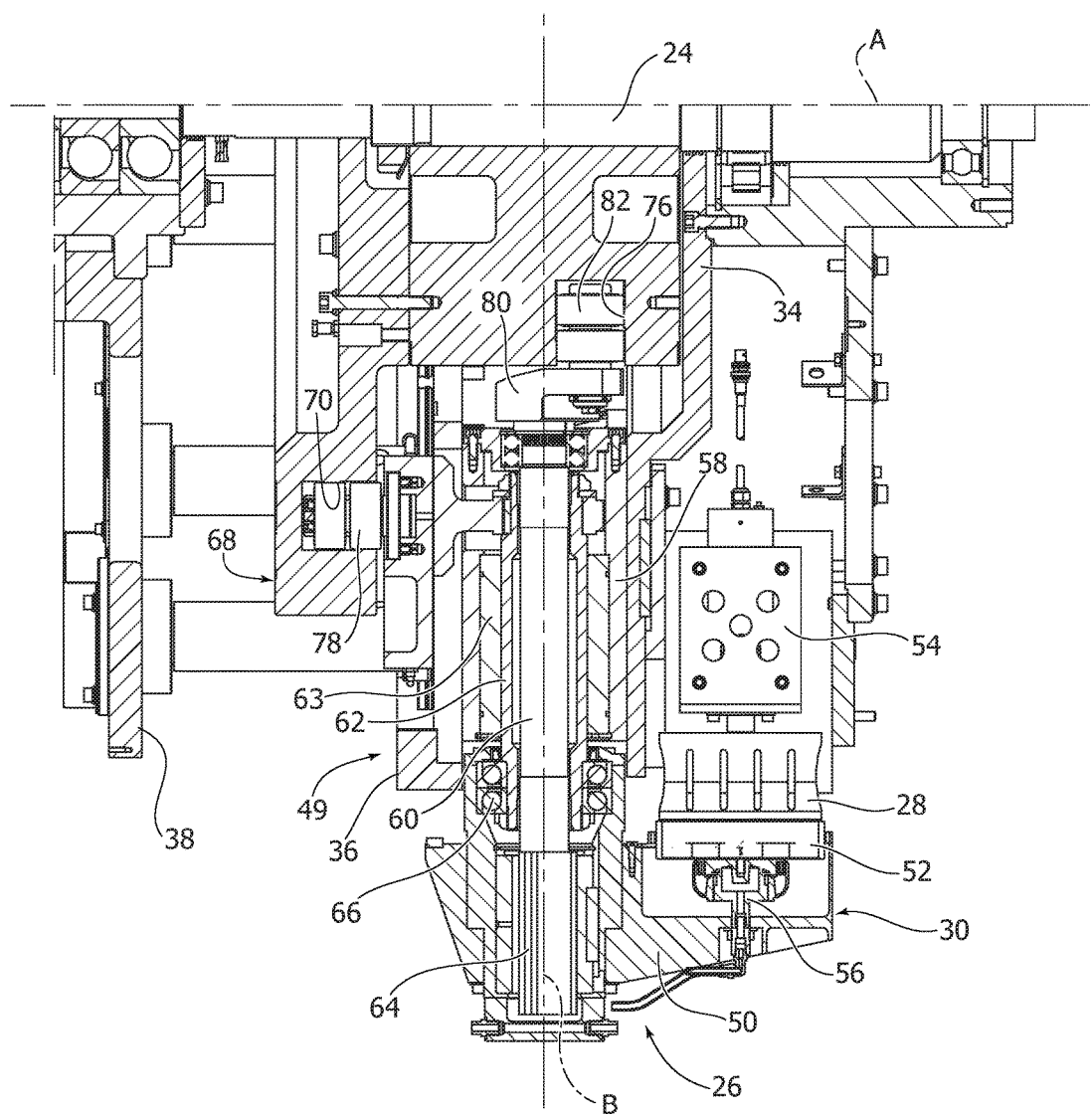
FIG. 4 is a cross-section along the line IV-IV of FIG. 1.

With reference to FIG. 4, each welding unit 26 comprises an actuating device 49, which controls the movement of the respective outer welding element 30 between the release position and the operative position, and vice versa. With reference to FIG. 4, the outer welding element 30 comprises a body 50, which carries an anvil 52 that cooperates with the inner welding element 28. In the illustrated example, the inner welding element 28 is a sonotrode connected to an ultrasound generator 54. The inner welding element 28 is preferably in a fixed position with respect to the rotary structure 14. Preferably, the anvil 52 of the outer welding element 30 is carried in a floating manner from the body 50, and a pneumatic actuator 56, arranged between the body 50 and the anvil 52, is provided, which pushes the anvil 52 towards the inner welding element 28.

Still with reference to FIG. 4, the actuating device 49 comprises a support 58 fixed to the second plate 36. The support 58 carries a shaft 60 that is rotatable with respect to the support 58 about a respective radial axis B. The shaft 60 is fixed with respect to the support 58 in the direction of the axis B. A tubular sleeve 62 is mounted coaxially with the shaft 60. The tubular sleeve 62 is movable in a linear direction in the direction of the axis B and is rotatably fixed with respect to the support 58. Preferably, a ball sleeve 63 is arranged between the support 58 and the tubular sleeve 62.

The shaft 60 has an outer end with a splined profile 64 on which the body 50 of the outer welding element 30 is engaged. The body 50 is rotatably fixed with respect to the shaft 60, and is movable with respect to the shaft 60 in the direction of the axis B by virtue of the sliding coupling by means of the splined profile 64. The body 50 of the outer welding element 30 is connected to the tubular sleeve 62 via a bearing 66. The body 50 of the outer welding element 30 is rotatable with respect to the tubular sleeve 62 about the axis B, and is fixed with respect to the tubular sleeve 62 in the direction of the axis B.

With reference to FIGS. 3 and 4, the welding apparatus 10 comprises a stationary cam element 68, which cooperates with the actuating devices 49 of the welding units 26. The stationary cam element 68 comprises a first cam 70 and a second cam 76.

With reference to FIG. 4, each actuating device 49 comprises a first cam follower 78 attached to the tubular sleeve 62, which engages the first cam 70 of the stationary cam element 68. The first cam 70 controls a linear movement of the tubular sleeve 62 in the direction of the axis B.

Still with reference to FIG. 4, the shaft 60 of each actuating device 49 is fixed to a lever 80, which carries a second cam follower 82 that engages the second cam 76 of the stationary cam element 68. The second cam 76 controls an angular rotation of the shafts 60 about the respective axes B.

The parts of the transmission mechanism 49 that control the angular rotation movement and the linear translation movement of the outer welding element 30 are independent of each other, so as to reduce the inertia of the rotating masses and the translating masses. In particular, the inertia of the rotating masses is given by the mass of the shaft and of the outer welding element 30. The inertia of the translating masses is given by the mass of the translating sleeve 62 and of the outer welding element 30. The division of the angular rotation movement and of the linear translation movement allows a reduction of the inertia masses of the two movements and, consequently, faster accelerations of the rotation and translation movements.

The profiles of the two cams 70, 76 are determined in order to provide coordinated angular rotation movements and linear translation movements of the outer welding elements 30. During rotation of the rotary structure 14, each outer welding element 30 moves cyclically from the release position to the operative position, and vice versa. In the release position, the anvil 52 of each outer welding element 30 is displaced in a radial direction outwards relative to the inner welding element 28, and is rotated by 90° relative to the operative position. Starting from the release position, during rotation of the rotary structure, the outer welding element 30 rotates angularly about the respective radial axis B, moving to a position in which the anvil 52 is aligned with the inner welding element 28. At the same time, the outer welding element 30 moves in a radial direction inwards. The contact of the anvil 52 with the tape occurs when the anvil 52 is already parallel with respect to the inner welding element 28. The anvil 52 and the inner welding element 28 clamp the tape between them with a movement in a rectilinear direction, parallel to the respective axis B. The contact between the inner welding element 28, the anvil 52 and the tape takes place uniformly along the welding line. The contact pressure between the inner welding element 28 and the anvil 52 is provided by the force with which the outer welding element 30 is pushed in the direction of the axis B. This force can be modulated by varying the feed pressure of the pneumatic actuator 56. The geometry of the movement of the outer welding element 30 causes the contact pressure to be substantially uniform along the welding line. The uniform contact pressure provides better guarantees of the welding quality.

The inner welding element 28 and the anvil 52 remain in contact with the tape T for a period of time sufficient to transfer the welding energy to the tape T. The welding is terminated before the welding unit 26 reaches the release area of the tape T from the rotary structure 14. At the end of the welding, the outer welding element 30 is first moved away in a radial direction with a movement in a straight direction in the direction of the axis B, in order to release the tape T. After release of the anvil 52 from the tape T, the outer welding element 30 is rotated by 90° towards the release position.

Of course, without prejudice to the principle of the invention, the details of construction and the embodiments can be widely varied with respect to those described and illustrated, without thereby departing from the scope of the invention as defined by the claims that follow.

The invention claimed is:

1. An apparatus for the transverse welding of a tape traveling in a machine direction, comprising:
   a stationary structure;
   a rotary structure rotatable with respect to the stationary structure about a rotation axis perpendicular to said machine direction; and
   a plurality of welding units carried by said rotary structure and spaced apart in a circumferential direction, wherein each of said welding units comprises an inner welding element fixed relative to the rotary structure, and an outer welding element cyclically movable with respect to the rotary structure, between a release position and an operative position, and vice versa and wherein each of said outer welding elements during the movement from said release position to said operative position, and vice versa, performs an angular rotation movement about a respective radial axis perpendicular to said rotation axis and a linear translation movement along said radial axis.

2. An apparatus according to claim 1, comprising a stationary cam element comprising a first cam and a second cam independent from each other, which control, respectively, the linear translation movement and the angular rotation movement of said outer welding elements.

3. An apparatus according to claim 2, wherein each of said welding units comprises a respective actuating device comprising a shaft rotatable around the respective radial axis and a tubular sleeve coaxial to said shaft and movable in a linear direction in the direction of the respective radial axis, said tubular sleeve and said shaft being connected to respective first and second cam followers that engage, respectively, said first cam and said second cam of said stationary cam element.

4. An apparatus according to claim 3, wherein each of said outer welding elements comprises a body rotationally connected to a respective shaft, and movable with respect to said shaft in the direction of the respective radial axis.

5. An apparatus according to claim 4, wherein said body of each of said outer welding elements is connected to the respective tubular sleeve via a bearing, so that said body is rotatable with respect to said tubular sleeve about the respective radial axis, and is connected to said tubular sleeve in the direction of the respective radial axis.

6. An apparatus according to claim 4, wherein each of said outer welding elements comprises an anvil connected in a floating manner to the respective body.

7. An apparatus according to claim 4, wherein between said body and said anvil of each of said outer welding elements, a pneumatic actuator is arranged, configured to push said anvil towards the respective inner welding element.

8. An apparatus according to claim 1, wherein said inner welding element is a sonotrode of an ultrasonic welding unit.

9. An apparatus according to claim 1, wherein said rotary structure comprises a perimeter wall carrying a plurality of suction chambers connected by respective conduits to a rotary distributor.

* * * * *